United States Patent
De Silva et al.

(10) Patent No.: US 7,544,332 B2
(45) Date of Patent: Jun. 9, 2009

(54) AIR TREATMENT DISPENSERS DELIVERING MULTIPLE CHEMICALS

(75) Inventors: Ranjit A. De Silva, Racine, WI (US); Brian T. Davis, Burlington, WI (US); Gopal P. Ananth, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 157 days.

(21) Appl. No.: 11/684,707

(22) Filed: Mar. 12, 2007

(65) Prior Publication Data

US 2008/0226493 A1    Sep. 18, 2008

(51) Int. Cl.
*A61L 9/03* (2006.01)

(52) U.S. Cl. .......................................... 422/125; 239/53

(58) Field of Classification Search .................... 239/53, 239/54, 55, 56
See application file for complete search history.

(56) References Cited

U.S. PATENT DOCUMENTS

| | | | |
|---|---|---|---|
| 4,128,508 | A | 12/1978 | Munden |
| 4,228,124 | A | 10/1980 | Kashihara et al. |
| 4,439,415 | A | 3/1984 | Hennart et al. |
| 4,824,827 | A | 4/1989 | Kelly et al. |
| 4,921,636 | A | 5/1990 | Traas |
| 5,111,477 | A | 5/1992 | Muderlak et al. |
| 5,139,864 | A | 8/1992 | Lindauer |
| 5,647,052 | A | 7/1997 | Patel et al. |
| 6,031,967 | A | 2/2000 | Flashinski et al. |
| 6,154,607 | A | 11/2000 | Flashinski et al. |
| 6,551,560 | B1 | 4/2003 | Flashinski et al. |
| 6,663,838 | B1 | 12/2003 | Soller |
| 6,773,679 | B2 | 8/2004 | Jaworski et al. |
| 6,790,670 | B2 | 9/2004 | Munagavalasa et al. |
| 6,834,847 | B2 | 12/2004 | Bartsch et al. |
| 6,925,252 | B2 | 8/2005 | Zhang et al. |
| 2004/0007787 | A1 | 1/2004 | Kvietok et al. |
| 2004/0151747 | A1 | 8/2004 | Davis et al. |
| 2005/0284852 | A1 | 12/2005 | David et al. |

FOREIGN PATENT DOCUMENTS

| | | |
|---|---|---|
| EP | 1356731 A1 | 10/2003 |
| GB | 748994 | 5/1956 |

OTHER PUBLICATIONS

U.S. Appl. No. 11/346,697, filed Feb. 3, 2006, J. Adair et al.
U.S. Appl. No. 11/359,090, filed Feb. 22, 2006, B. Davis et al.
U.S. Appl. No. 11/379,495, filed Apr. 20, 2006, J. Adair et al.

*Primary Examiner*—Elizabeth L McKane

(57) ABSTRACT

Devices for dispensing air treatment chemicals are described. They have a first substrate bearing a first volatile air treatment chemical that is dispensed when the first substrate is heated, and a second substrate bearing a second volatile air treatment chemical that is dispensed from the second substrate when the second substrate is heated. The substrates are positioned in stacked fashion relative to each other, optionally with a permeable membrane there between. There may also be a use-up cue indicator unit coordinated with use of the chemicals. The first and second substrates and indicator unit can be in a single replaceable cartridge unit, preferably with the second substrate in the form of a porous ring that houses the indicator unit.

13 Claims, 6 Drawing Sheets

AIR TREATMENT DISPENSERS DELIVERING MULTIPLE CHEMICALS

CROSS-REFERENCE TO RELATED APPLICATIONS

Not applicable.

STATEMENT REGARDING FEDERALLY SPONSORED RESEARCH/DEVELOPMENT

Not applicable.

BACKGROUND OF THE INVENTION

The present invention relates to devices that dispense a plurality of volatile air treatment chemicals by heating at least one substrate impregnated with, or coated with, the chemicals, and that can also include indicators to indicate when the treatment chemical(s) have been used up.

Substrates (particularly porous substrates) have previously been used as carriers for air treatment chemicals such as insect control active ingredients, fragrances and deodorizers. See e.g. U.S. Pat. Nos. 5,111,477; 5,647,052, 6,551,560 and 6,663,838. "Insect control active ingredients" includes insecticides, insect repellants or attractants, insect growth inhibitors, and other materials that affect the behavior or development of insects and other arthropods commonly controlled with insects. The disclosure of these patents, and of all other patents, patent applications, patent application publications, and other documents referred to herein, are incorporated by reference as if fully set forth herein. Upon heating the substrate, a volatile air treatment chemical is caused to be dispensed from the substrate. The heating source is typically an electrical heater, but may instead employ combustion of a fuel.

With sufficient use the chemicals are eventually depleted. This depletion time frame is typically much shorter for the chemicals than the useful life of the rest of the device, particularly the electrical heating element and associated housing and electrical connector. Consequently, there has been designed a variety of devices that allow for a chemical reservoir refill unit to be replaced. See generally U.S. patent application Ser. No. 11/346,697 filed Feb. 3, 2006; Ser. No. 11/359,090 filed Feb. 22, 2006; and Ser. No. 11/379,495 filed Apr. 20, 2006. The disclosure of these applications are incorporated by reference as if fully set forth herein. Such devices permit replacement of a subassembly that holds the chemical to be dispensed to the air, and/or a use-up cue indicator, thereby eliminating the need to replace the heating subassembly.

Such devices have significantly advanced the art. However, they are primarily designed for situations where a single air treatment chemical is dispensed from one dispenser, and a use-up cue chemical is volatized from another. For example, a desirable insecticide or insect repellent may not have an optimal fragrance. Hence, it may be desirable to simultaneously mask or improve the smell of the insecticide by also delivering a fragrance to the air. However, the structure for controlling delivery of the primary insecticide may not be optimized for desirable fragrances, and mixing the fragrance with the use-up cue for dispensing therewith may complicate the coordination of the use-up cue chemical with use of the primary active.

Thus, a need exists for improved air treatment devices where a second chemical (apart from the primary active and the use-up cue) can be dispensed in a more efficient manner.

BRIEF SUMMARY OF THE INVENTION

In one aspect the invention provides an air treatment chemical dispensing system. It has a first substrate bearing a first volatile air treatment chemical capable of being dispensed from the first substrate when the first substrate is heated, and a second substrate bearing a second volatile air treatment chemical capable of being dispensed from the second substrate when the second substrate is heated. The second substrate is in the form of a porous structure (e.g. a porous ring) stacked adjacent to the first substrate. The second substrate shall be understood to be "stacked" adjacent to the first substrate if, in relation to a heat source for volatilizing the volatile air treatment chemicals, it is either located immediately beside or above the first substrate. The first and second substrates can be separated from each other by a sealing layer to prevent premature migration of active between the substrates (which sealing layer can be, by way only of example, a non-porous membrane, a coating applied to one or both of the substrates, or a modification in the surface structure of a substrate so as to seal it), and otherwise the substrates can be positioned relative to each other such that when the first substrate is dispensing the first volatile air treatment chemical, heat from the first substrate is capable of passing through the second substrate, whether by conduction through the second substrate or via an opening or other pathway (e.g. to reach an indicator unit).

In preferred forms the porous structure is made of porous polyethylene, and has a ring shaped body having an annular channel and a frustum shaped cavity radially inward of the annular channel. The frustum shaped cavity may be linked to an axial passageway extending to an outer surface of the second substrate.

In some forms there is also an indicator unit holding a volatile indicator chemical separate from both the first volatile air treatment chemical and the second volatile air treatment chemical, preferably housed in a cavity of the second substrate. The first substrate, the second substrate and the indicator unit are all mounted as part of a single replaceable cartridge refill unit.

The first air treatment chemical can be an insect control active ingredient such as transfluthrin, which impregnates a substrate made of sand and resin binder, and the second air treatment chemical can be a fragrance such as limonene impregnating a polyethylene second substrate. Alternatively, the second substrate can be impregnated with a synergist such as piperonyl butoxide.

These structures are designed to be used with heaters. The first substrate can be positioned proximate the heater such that the first substrate is sandwiched between the heater and the second substrate.

The indicator unit is to be coordinated with the rate of use-up of at least one of the volatile chemicals, preferably the volatile impregnating the first substrate. The indicator unit may include a transparent material that houses an indicator chemical. The disappearance of a volatile gel through a permeable membrane (as the gel volatizes) serves as the use-up indicator function. Alternatively, the second substrate can be treated directly with a dye or other material that changes appearance over time in coordination with the volatilization of either or both of the first or second air treatment chemicals, thus providing a visual cue that can be related to the exhaustion of either or both of the first or second volatile air treatment chemicals.

Systems of the present invention are particularly of interest where the two volatile air treatment chemicals are incompatible for long term storage (if mixed together prior to storage).

This could be because the two chemicals adversely react with each other, or because the optimal storage environments for each are not the same, or if shelf life decreases when the chemicals are mixed. It may also be desirable where the volatilization characteristics of these chemicals are so different that coordinating their dispensing is difficult if they are volatized from a mixed batch.

The foregoing and other advantages of the present invention will be apparent from the following description. In the description that follows reference is made to the accompanying drawings, which form a part thereof and in which there is shown by way of illustration, and not limitation, expected preferred embodiments of the invention. Such embodiments do not necessarily represent the full scope of the invention, and reference should therefore be made to the claims herein for interpreting the scope of the invention.

DETAILED DESCRIPTION OF THE PREFERRED EMBODIMENTS

Figure 1:
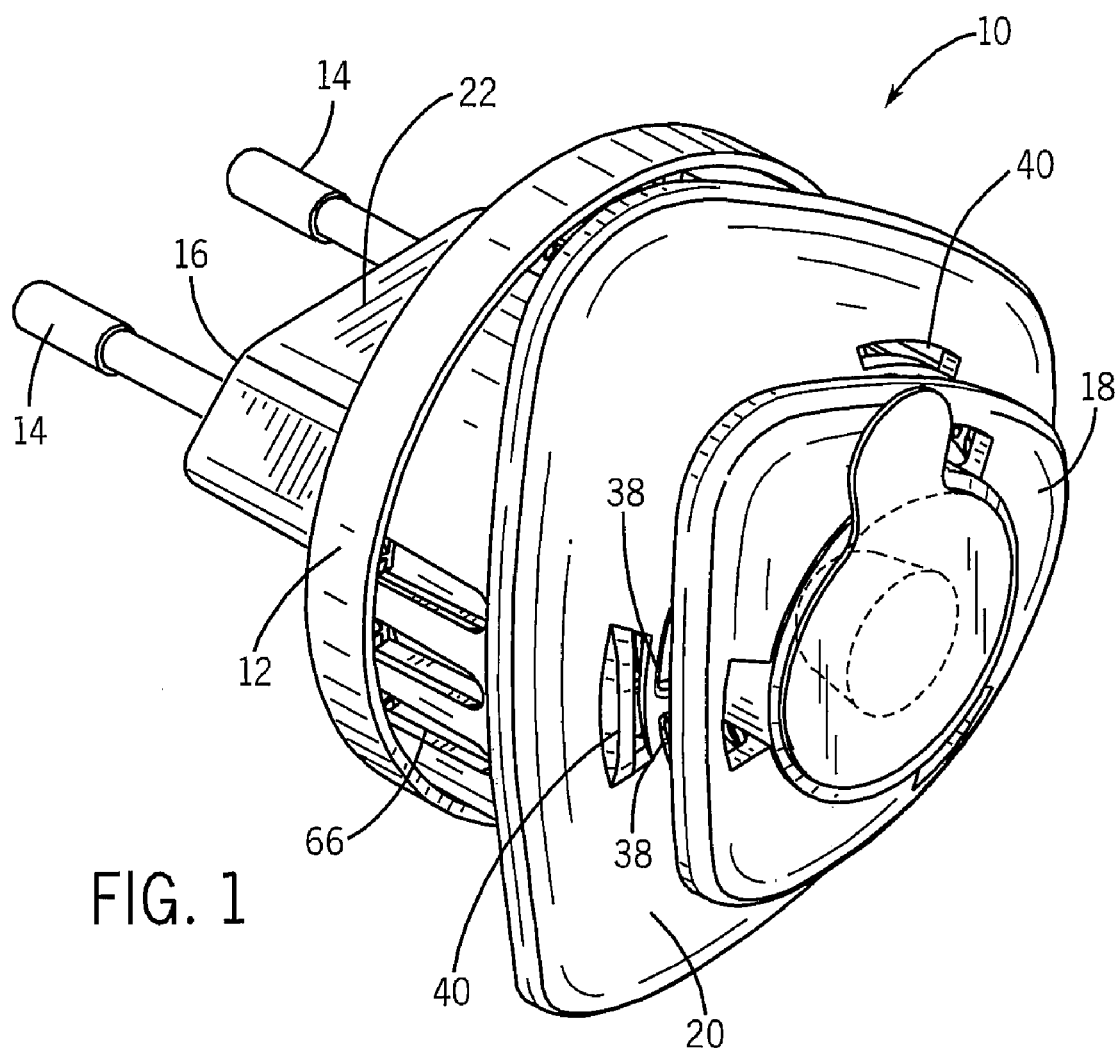
FIG. 1 is a perspective view of a preferred embodiment of an air treatment device of the present invention, with a refill cartridge slightly exploded from the device housing.
Figure 2:
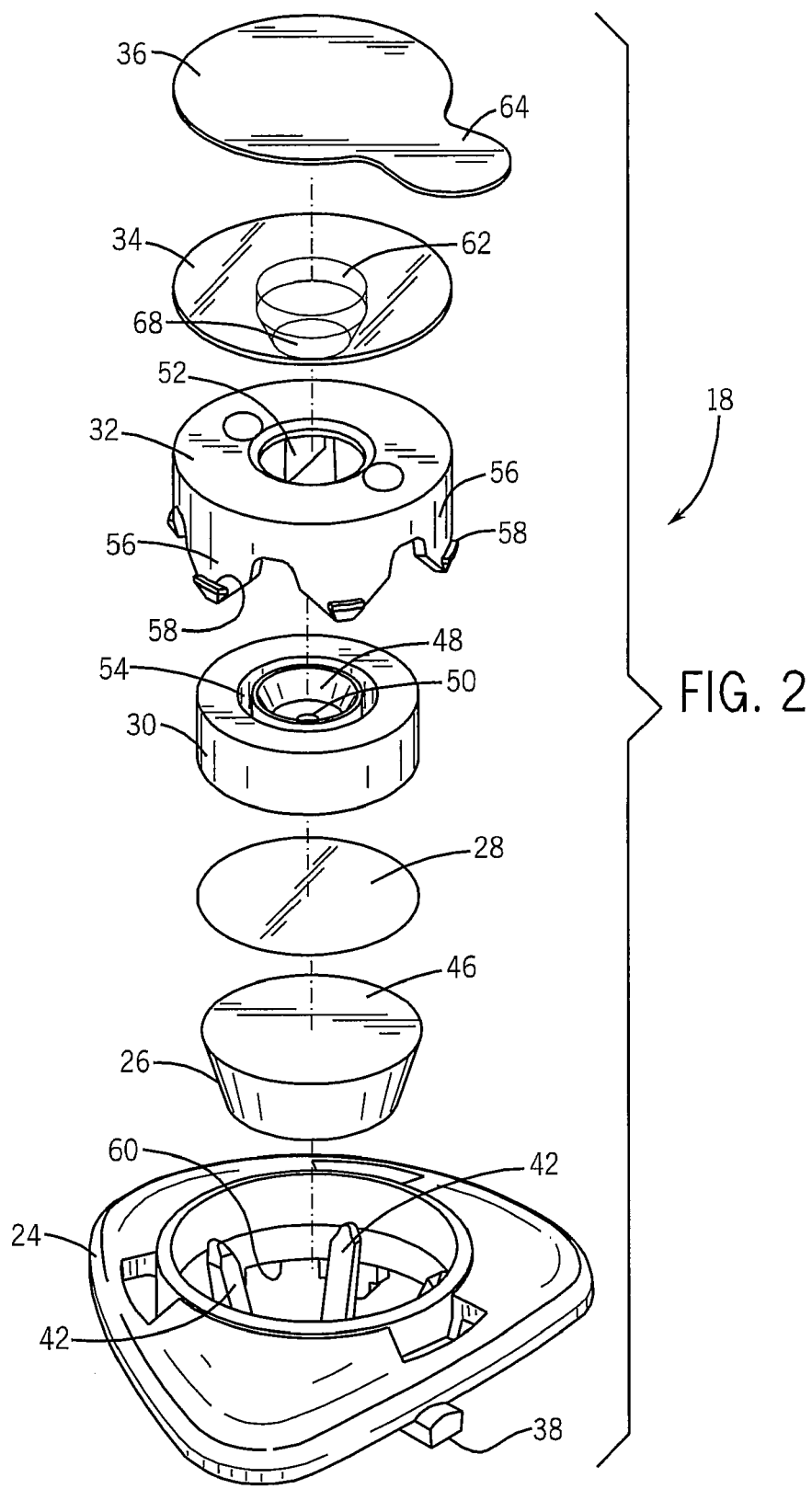
FIG. 2 is an exploded perspective view of the refill cartridge of FIG. 1.
Figure 3:
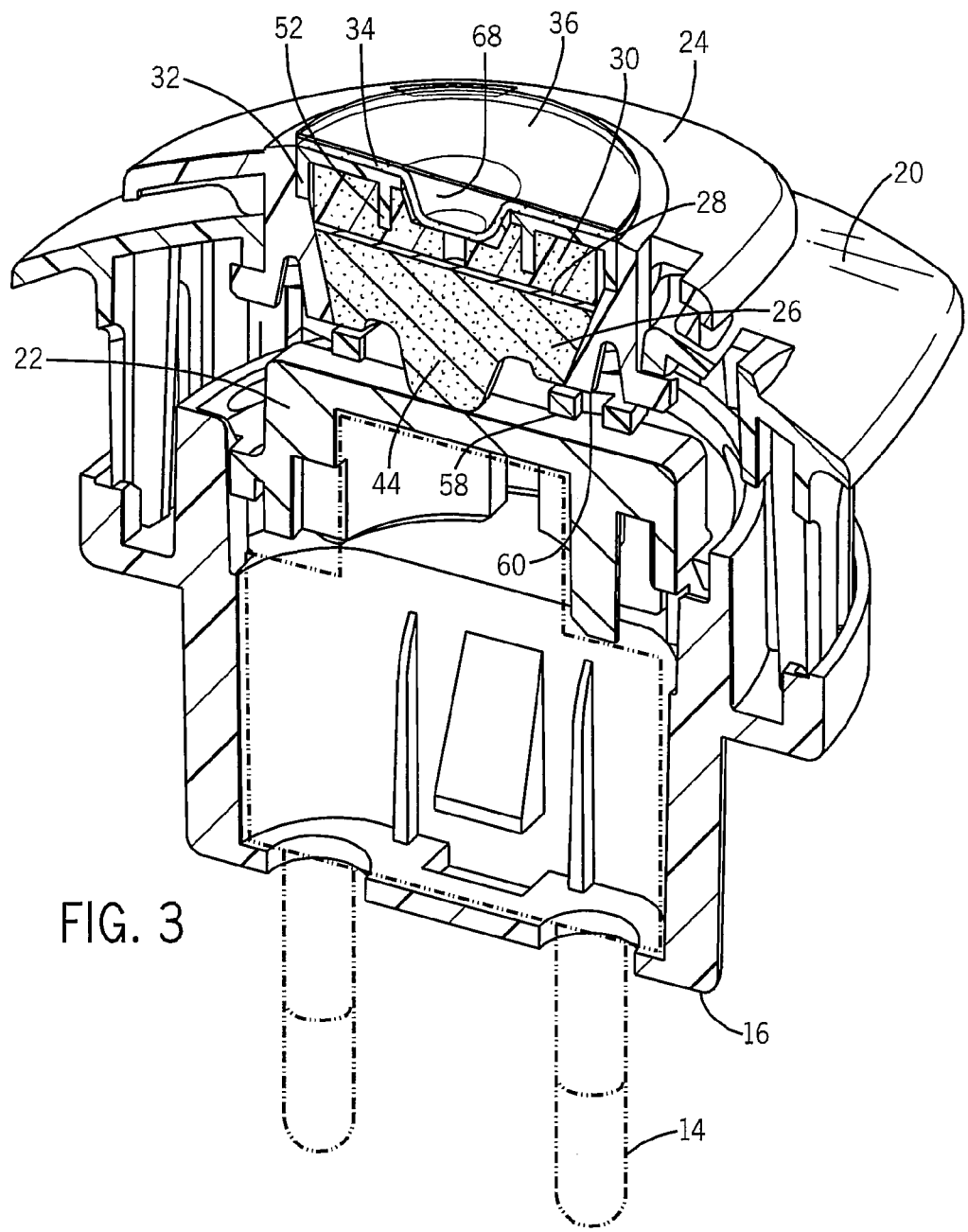
FIG. 3 is cross-sectional perspective view of the embodiment of FIG. 1, taken approximately along the center line of the plug prongs.

Referring first to FIGS. 1-3, a first preferred embodiment of an air treatment chemical dispensing device 10 is shown. The device 10 has a housing 12 having electrical prongs 14 at a rear end 16 and a refill cartridge unit 18 at an opposing forward end 20. Electrical prongs 14 are electrically connected to heater 22. An embodiment of a preferred table-shaped heater 22 is more fully disclosed in U.S. patent application Ser. No. 11/359,090 filed Feb. 22, 2006.

The device is most preferably plugged into an electric socket on a vertical wall. Hence, the directional terms in this patent are used with that type of installation in mind. However, appropriate electric sockets on horizontal or other surfaces may also be used to provide power. Thus, the terms such as "front", "rear", "upper", "lower", and "side" should be interpreted in an analogous manner when the devices are used for that type of installation.

The shape of the prongs 14 shown in the figures are merely for purposes of example. Cylindrical prongs of this type are suitable for linking to electric power in some countries. However, in other countries blade prongs, or mixtures of blades, cylinders and other shaped prong elements will be used to supply the linkage to the available power (as is well recognized in the art).

Turning now to cartridge unit 18, there is a cartridge housing 24, a first substrate 26 bearing a first volatile air treatment chemical capable of being dispensed from first substrate 26 when first substrate 26 is heated, a membrane 28, a second substrate 30 bearing a second volatile air treatment chemical capable of being dispensed from second substrate 30 when second substrate 30 is heated, a substrate clasp 32, an indicator unit 34 holding a volatile indicator chemical separate from either the first volatile air treatment chemical or the second volatile air treatment, and a peel-off lid 36 which is removable from indicator unit 34.

Cartridge housing 24 includes clips 38 which easily connect to and disconnect from device housing 12 at recesses 40, making cartridge unit 18 easily replaceable when the volatile chemicals are depleted. Columns 42 confine first substrate 26, and certain other elements of cartridge unit 18.

First substrate 26 can be a sand core plug with a frustum shaped nose 44 contacting heater 22 at one side, having a planar surface 46 at the opposed side. Substrate 26 is impregnated with a volatile air treatment chemical capable of being dispensed from substrate 26 when substrate 26 is heated. As an alternative to being completely impregnated with the air treatment chemical, substrate 26 may instead be only partially impregnated, or instead merely be coated with that chemical, or some combination thereof.

The substrate 26 can be fabricated from any material that is capable of absorbing the volatile air treatment chemical, remaining essentially stable under heating conditions, and releasing the air treatment chemical under heating conditions. Examples of a suitable substrate 26 include but are not limited to porous sand with a binder such as novolac resin, urethane resins and highly cross linked thermoplastics such as cross linked polyethylene. Particularly preferred sand substrates can be made in a fashion analogous to the sand wicks described in U.S. patent application publication 2005/0284952. Alternative substrates include cellulose, glass fiber filters, synthetic paper materials, ceramic materials, textiles, felt-type materials, wovens and nonwovens, bonded or sintered synthetics, natural polymer powders, and the like.

Membrane 28 can be a material, such as polyethylene terephthalate, that provides a barrier which blocks any material transfer between substrates 26 and 30. Membrane 28 in any event allows efficient heat transfer between substrates 26 and 30 so that substrates 26 and 30 can be heated concurrently when heater 22 is on. In effect, membrane 28 provides a sealing layer to resist transfer of material between substrates 26 and 30. As noted, above, the sealing layer may alternatively be a sprayed-on or otherwise applied layer of an epoxy varnish or any other material that can be applied to the surface of either substrate 26 or 30 to prevent such a transfer of material, or it may be a melting or other modification of the surface of either substrate sufficient to seal the substrate.

Figure 4:
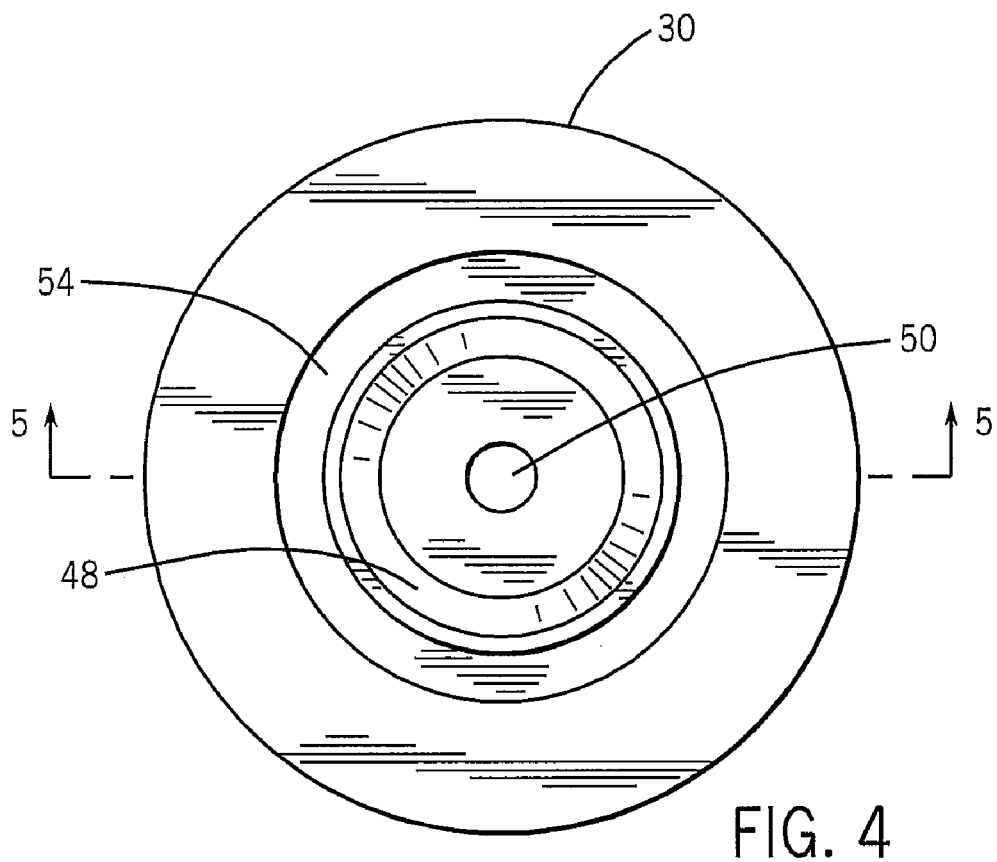
FIG. 4 is a top view of a porous ring substrate of FIG. 1.
Figure 5:
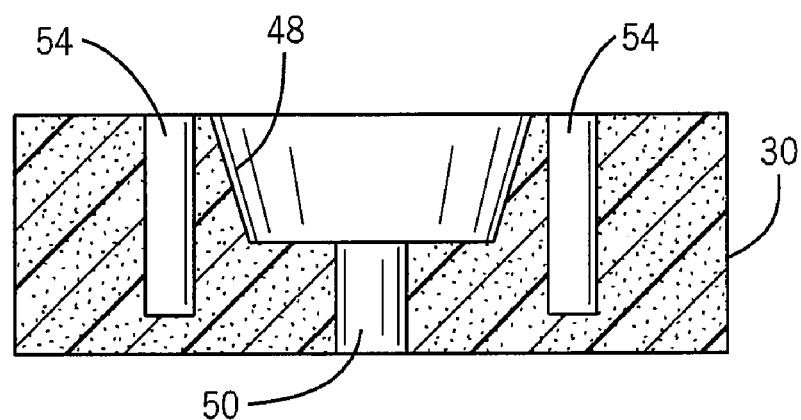
FIG. 5 is a cross-sectional view taken along line 5-5 of FIG. 4.

As is evident from FIGS. 2, 4 and 5, second substrate 30 is in the form of a porous ring which has a depression 48, in the form of a frustum shape, and in its top to accept indicator unit 34. Depression 48 extends deeply into the porous ring and preferably has an opening 50 in the form of an axial pathway in the floor of depression 48. This allows indicator unit 34 to still be directly exposed to the planar surface 46 of sand core substrate 26 so that indicator unit 34 is heated more efficiently as substrate 26 gets hot. This occurs by reducing the insulating effect of substrate 30.

Downwardly extending tabs 52 of substrate clasp 32 are inserted into an annular downwardly opening channel 54 in substrate 30. Second substrate 30 may alternatively be comprised of any material that is capable of absorbing the volatile air treatment chemical, remaining essentially stable under heating conditions, and releasing the air treatment chemical under heating conditions, such as those described above with respect to substrate 26. As with substrate 26, substrate 30 is impregnated with a volatile air treatment chemical, or alternatively to being completely impregnated with the air treatment chemical, substrate 30 may instead be only partially impregnated, or instead merely be coated with that chemical, or some combination thereof.

Substrate clasp 32 includes tabs 56 with lands 58 which spring under surface 60 of cartridge housing 24 thereby firmly holding first substrate 26, membrane 28, and second substrate 30 to cartridge housing 24.

Preferably, first substrate 26 includes a first volatile air treatment chemical that is an insecticide and second substrate 30 includes a second volatile air treatment chemical that is a fragrance. However, either the first volatile air treatment chemical and/or the second volatile air treatment chemical can include an insect control active ingredient, fragrance, deodorant or other types of chemicals. When the first and/or second volatile air treatment chemical is an insect control active ingredient, organic phosphorous insecticides, lipidamide insecticides, natural repellents as citronella oil, natural pyrethrins and pyrethrum extract, and synthetic pyrethroids are preferred. Suitable synthetic pyrethroids are acrinathrin, allethrin as D-allethrin, PynaminR™, benfluthrin, bifenthrin, bioallethrin as Pynamin ForteR™, S-bioallethrin, esbiothrin, esbiol, bisoresmethrin, cycloprothrin, cyfluthrin, beta-cyfluthrin, cyhalothrin, lambda-cyhalothrin, cypermethrin, alpha-cypermethrin, beta-cypermethrin, cyphenothrin, deltamethrin, empenthrin, esfenvalerate, fenpropathrin, fenvalerate, flucythrinate, taufluvalinate, kadethrin, permethrin, phenothrin, prallethrin as EtocR™, resmethrin, tefluthrin, tetramethrin, tralomethrin, or transfluthrin. Other volatile insecticides, such as those described in U.S. Pat. No. 4,439, 415, can also be employed.

In particularly preferred versions, the volatile insecticide is selected from the group consisting of transfluthrin, metofluthrin, vapothrin, permethrin, prallethrin, tefluthrin and esbiothrin. Transfluthrin is the most preferred insecticide.

Optional solvents for carrying these air treatment chemicals include, but are not limited to, ISOPAR™ C, ISOPAR™ E, ISOPAR™ L, heptane, methanol, acetone, ethanol, isopropyl alcohol, dodecene and tetrahydrofuran. ISOPAR™ C, ISOPAR™ E and ISOPAR™ L are hydrocarbon solvents of varying chain length and are available from Exxon Chemical Company, and are particularly preferred.

Nevertheless, it is preferred to apply transfluthrin for mosquito control without solvent. The transfluthrin can be heated to about 60° C. and applied to a porous substrate such as a sand substrate.

Either the first volatile air treatment chemical and/or the second volatile air treatment chemical can include a wide variety of volatile fragrances that may optionally also have insect control attributes. Alternatively, some fragrances may be selected that provide a deodorizing function (e.g. certain terpenes). For example, various natural and artificial perfumes may be used. Non-limiting examples of these perfumes include animal-based and plant-based natural perfumes, and artificial perfumes such as alcohols, phenols, aldehydes, ketones, terpenes, and esters.

When a volatile air treatment chemical is a disinfectant, preferred disinfectants include, but are not limited to, glycols, trimethylene and dipropylene. Organic acids compatible with the use of the substrates 26 and 30 and the environment may also be used.

Indicator unit 34 holds a volatile indicator chemical separate from either the first volatile air treatment chemical or the second volatile air treatment, and can be as described by U.S. patent application Ser. No. 11/346,697 filed Feb. 3, 2006. Dispensing of an air treatment chemical is indicated by a visible cue whose appearance results from the dispensing of an indicator chemical associated with an indicator unit 34.

For example, a peel-off lid 36 can be removable from the indicator unit 34, exposing the permeable membrane 62 covering the indicator chemical to the environment (as the chemical may diffuse past the permeable membrane once the lid is removed). The lid has a tab section 64 to facilitate gripping of the peel-off lid 36. Once the lid is removed indicator operation is initiated because this allows the volatile indicator chemical to escape to the environment upon heating.

The indicator chemical can be any material that provides a visual cue when exposed to heating that it is being heated. In a preferred version, the indicator chemical is in the form of a liquid or, alternatively, a gel or other semi-solid material. Other fluid-based compounds may also be used.

Particularly preferred volatile indicator chemicals are those guaiazulene dye materials described in U.S. Pat. No. 6,790,670 (which is hereby incorporated by reference as if fully set forth herein). It should also be noted that the U.S. Pat. No. 6,790,670 patent describes a variety of ways of more precisely controlling the speed of volatilization of such dyes (e.g. using retarders and solvents, among other means).

Apart from the preferred indicator system it should be understood that (as taught in U.S. Pat. No. 6,031,967, hereby incorporated by reference as if fully set forth herein) a wide variety of materials are known to slowly permeate out of a unit when heated or otherwise allowed to vaporize. Such a material, whether held in a separate structure associated with the second substrate 30 or even directly applied to the second substrate, could function as a visual use-up cue if so arranged that a consumer could see the disappearance of that material. If such a material is applied directly to the second substrate 30, it will be apparent that the depression 48 may then not be necessary.

The heating element is preferably activated by inserting the electrical prongs 14 into an outlet (not shown). The housing 12 has a series of elongated vents 66 on the upper and lower sides of housing 12. Vents 66 allow in air from the environment and permit it to pass along with the air treatment chemicals dispensed from substrate 26 and at least partially from substrate 30 through the vent openings on the upward side of the housing. It should be noted that the nose 44 of the substrate 26 is preferably positioned closely adjacent the heater with room around the nose for air to pass completely around its periphery. Heat from the heater 22 is also permitted to pass against other surfaces of the cartridge unit 18 through a variety of openings of device 10.

The indicator unit 34 is removable from the cartridge unit 18, thus allowing the indicator unit 34 to be replaced separately from the substrates 26 and 30. Alternatively, the indicator unit 34 may be replaced along with the rest of the cartridge unit.

The indicator unit 34 may also contain another air treatment chemical in addition to the indicator chemical. The other volatile air treatment chemical may be combined with the indicator chemical in the cup-shaped well 68.

As the indicator chemical is heated (and dispensed into the environment) a visible cue results in that one will be able to see that the chemical is disappearing (or at some point has completely disappeared). When a consumer sees this they will know that the end of utility is near, and then know that the substrates 26 and/or 30 are essentially used up. By "use-up cue" it is meant either that an extent of use is indicated, or that completion of use is indicated.

Where the indicator volatile is colored, a portion of the visible cue may be a color change. Moreover, a thermochromic dye (such as copper mercury iodide) may be added to the indicator volatile that changes color when heated. In a preferred version, the thermochromic dye changes from a first color to a second color when heated, and then returns to the first color upon subsequent cooling, to thereby provide a visible off/on/off cue.

Figure 6:
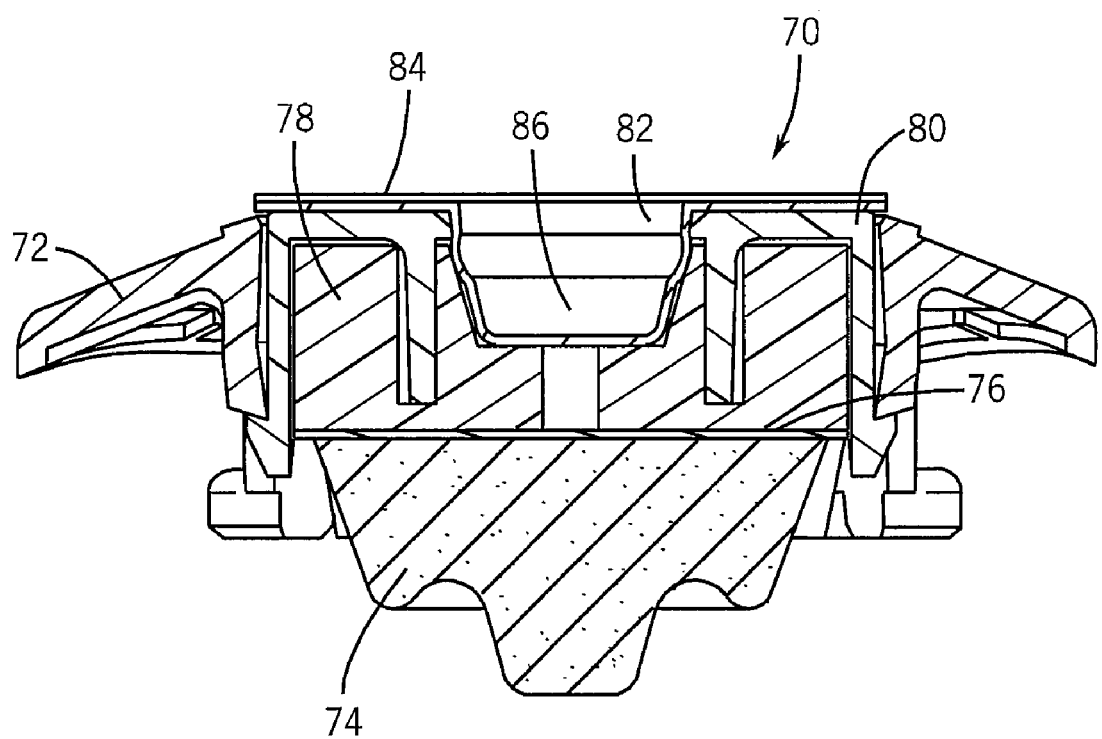
FIG. 6 is a cross-sectional view of another embodiment of the cartridge unit.
Figure 7:
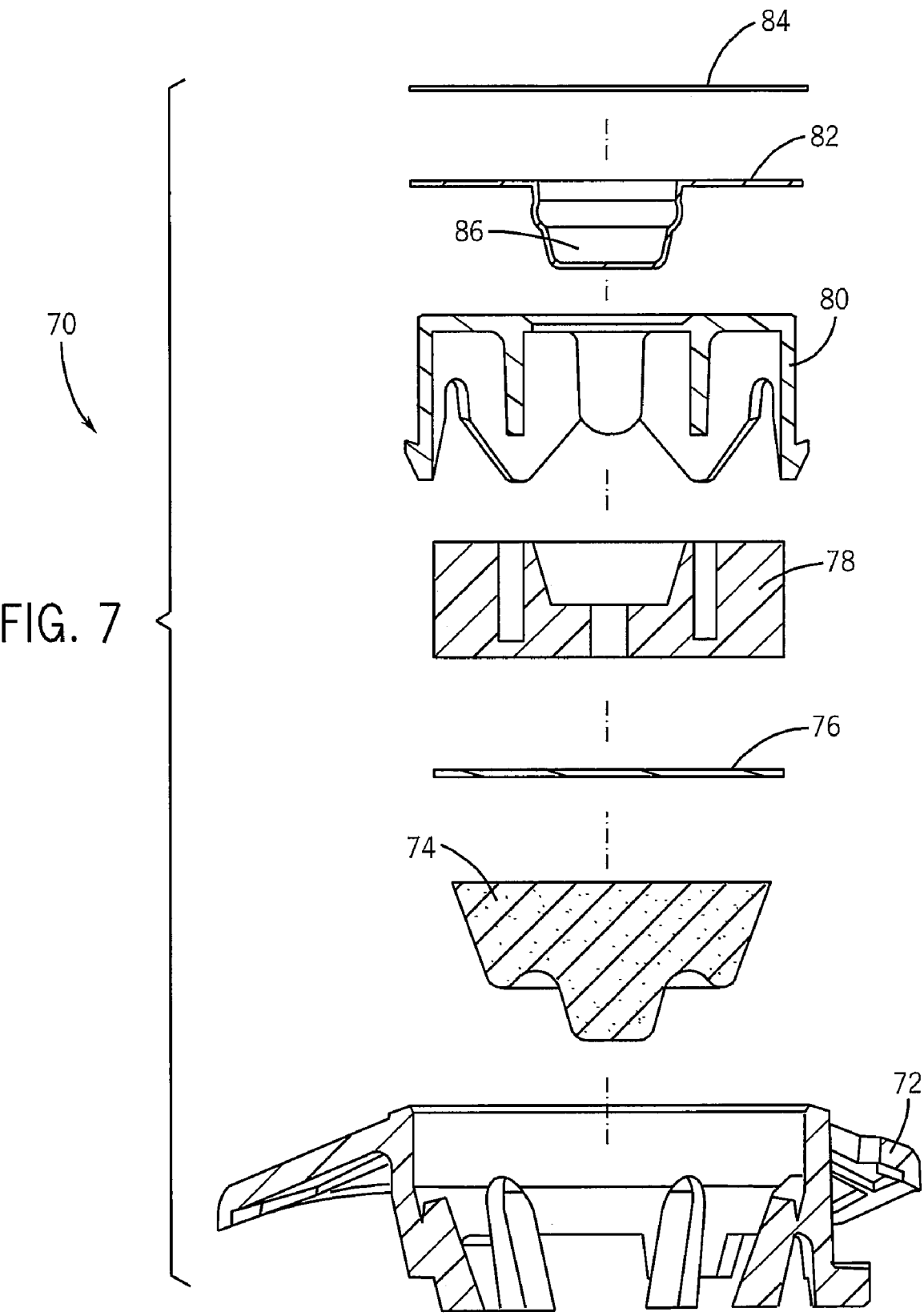
FIG. 7 is an exploded cross-sectional view of the cartridge unit of FIG. 6.

The embodiment of FIGS. 6 and 7 illustrate an alternative cartridge unit 70, which in many ways is similar to cartridge unit 18, which can be used with device 10 instead of cartridge unit 18, and which includes cartridge housing 72, a first substrate 74 bearing a first volatile air treatment chemical capable of being dispensed from first substrate 74 when first substrate 74 is heated, a membrane 76, a second substrate 78 bearing a second volatile air treatment chemical capable of being dispensed from second substrate 78 when second substrate 78 is heated, a substrate clasp 80, an indicator unit 82 holding a volatile indicator chemical separate from either the first volatile air treatment chemical or the second volatile air treatment, and a peel-off lid 84 that is removable from indicator unit 82. The function and other attributes of cartridge unit 70 are similar to cartridge unit 18, as are the chemicals, with only minor differences in proportion in some elements such as well 86 of indicator unit 82.

While preferred embodiments of the present invention have been described above, it should be appreciated that the invention could be applied to a variety of other embodiments. For example, it is not critical that the indicator well be mounted directly onto the removable cartridge that carries the substrate. In this regard, the substrate(s) can be separately positioned on the heating device, and the substrate(s) can be configured in a variety of geometries.

Thus, the principles of the present invention can be applied in a variety of other ways apart from those specifically noted herein and/or depicted in the drawings. Still other modifications may be made without departing from the spirit and scope of the invention. Thus, the claims (rather than just the preferred embodiments) should be reviewed in order to understand the full scope of the invention.

INDUSTRIAL APPLICABILITY

Disclosed are air treatment devices with multiple substrates for dispensing multiple volatile air treatment chemicals, and/or with visual use-up cue capabilities.

What is claimed is:

1. An air treatment chemical dispensing system, comprising:
    a first substrate bearing a first volatile air treatment chemical capable of being dispensed from the first substrate when the first substrate is heated;
    a second substrate bearing a second volatile air treatment chemical capable of being dispensed from the second substrate when the second substrate is heated;
    an indicator unit holding a volatile indicator chemical separate from both the first volatile air treatment chemical and the second volatile air treatment chemical;
    wherein the second substrate is in a form of a porous structure stacked over the first substrate and has an opening in the form of an axial pathway;
    wherein the indicator unit is stacked over the second substrate; and
    wherein the dispensing system is configured such that heat from the first substrate is able to pass through the axial pathway of the second substrate to the indicator unit.

2. The air treatment chemical dispensing system of claim 1, wherein the porous structure is a porous ring.

3. The air treatment chemical dispensing system of claim 1, wherein the first and second substrates are positioned relative to each other such that when the first substrate is dispensing the first volatile air treatment chemical, heat from the first substrate is capable of passing through the axial pathway through the second substrate to the indicator unit.

4. The air treatment chemical dispensing system of claim 1, wherein the porous structure is comprised of polyethylene.

5. The air treatment chemical dispensing system of claim 1, wherein the indicator unit is housed in a cavity of the second substrate.

6. The air treatment chemical dispensing system of claim 5, wherein the first substrate, the second substrate and the indicator unit are all mounted as part of a single replaceable cartridge refill unit.

7. The air treatment chemical dispensing system of claim 1 wherein the second substrate is treated directly with a material that changes appearance over time in coordination with the volatilization of either or both of the first or second air treatment chemicals.

8. The air treatment chemical dispensing system of claim 1, wherein the first volatile air treatment chemical is an insect control active ingredient and the second volatile air treatment chemical is fragrance.

9. The air treatment chemical dispensing system of claim 1, wherein the first volatile air treatment chemical is an insect control active ingredient and the second volatile air treatment chemical is a synergist for the insect control active ingredient.

10. The air treatment chemical dispensing system of claim 1, further including a heating element, the first substrate being positioned proximate the heating element such that the first substrate is sandwiched between the heating element and the second substrate.

11. An air treatment chemical dispensing system, comprising:
    a first substrate bearing a first volatile air treatment chemical capable of being dispensed from the first substrate when the first substrate is heated;
    a second substrate bearing a second volatile air treatment chemical capable of being dispensed from the second substrate when the second substrate is heated;
    an indicator unit holding a volatile indicator chemical separate from both the first volatile air treatment chemical and the second volatile air treatment chemical;
    wherein the second substrate is in a form of a porous structure stacked over the first substrate;
    wherein the indicator unit is stacked over the second substrate; and
    wherein the dispensing system is configured such that heat from the first substrate is able to pass through the second substrate to the indicator unit;
    wherein the porous structure is a porous ring; and
    wherein the first and second substrates are separated by a sealing layer sufficient to resist transfer of the volatile of either of the substrates to the other substrate.

12. An air treatment chemical dispensing system, comprising:
    a first substrate bearing a first volatile air treatment chemical capable of being dispensed from the first substrate when the first substrate is heated; and
    a second substrate bearing a second volatile air treatment chemical capable of being dispensed from the second substrate when the second substrate is heated;
    wherein the second substrate is in a form of a porous structure stacked adjacent to the first substrate;
    wherein the porous structure is a porous ring; and
    wherein the porous structure comprises a ring shaped body having an annular channel and a frustum shaped cavity radially inward of the annular channel.

13. The air treatment chemical dispensing system of claim 12, wherein the frustum shaped cavity is linked to an axial passageway extending to an outer surface of the second substrate.

* * * * *